United States Patent
Geddes et al.

(10) Patent No.: US 7,164,938 B2
(45) Date of Patent: Jan. 16, 2007

(54) OPTICAL NONINVASIVE VITAL SIGN MONITOR

(75) Inventors: Leslie A. Geddes, Lafayette, IN (US); Rebecca A. Roeder, Lafayette, IN (US); Kirk S. Foster, West Lafayette, IN (US); George P. Graber, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 11/157,215

(22) Filed: Jun. 20, 2005

(65) Prior Publication Data

US 2005/0283082 A1 Dec. 22, 2005

Related U.S. Application Data

(60) Provisional application No. 60/581,584, filed on Jun. 21, 2004.

(51) Int. Cl.
*A61B 5/00* (2006.01)
*A61B 5/02* (2006.01)

(52) U.S. Cl. .................. 600/324; 600/344; 600/499

(58) Field of Classification Search ............ 600/310, 600/322–324, 340, 344, 483, 485, 499, 502, 600/529
See application file for complete search history.

(56) References Cited

U.S. PATENT DOCUMENTS

| | | | |
|---|---|---|---|
| 3,858,574 A | 1/1975 | Page | |
| 3,978,849 A | 9/1976 | Geneen | |
| 4,202,347 A | 5/1980 | Sacks | |
| 4,469,107 A | 9/1984 | Asmar et al. | |
| 4,539,997 A * | 9/1985 | Wesseling et al. | 600/480 |
| 4,543,962 A | 10/1985 | Medero et al. | |
| 4,638,810 A | 1/1987 | Ramsey et al. | |
| 4,685,464 A | 8/1987 | Goldberger et al. | |
| 4,726,382 A * | 2/1988 | Boehmer et al. | 600/480 |
| 4,754,406 A | 6/1988 | Miyawaki et al. | |
| 4,830,014 A | 5/1989 | Goodman et al. | |

(Continued)

FOREIGN PATENT DOCUMENTS

EP 0276344 A1 8/1988

(Continued)

OTHER PUBLICATIONS

BioSpace article on Nellcor MAX-FAST Forehead Sensor.

(Continued)

*Primary Examiner*—Eric F. Winakur
(74) *Attorney, Agent, or Firm*—William F. Bahret

(57) ABSTRACT

An optical noninvasive vital sign monitor comprising a reflectance-type optical sensor within a pressurizable capsule retained by a headband, the capsule having an optically transparent or translucent inner wall adapted for placement against a subject's forehead. The optical sensor is mounted on the inside surface of the pressurizable capsule's inner wall, which contacts the subject's forehead during use, and includes a light source and a photodetector aimed toward the inside surface of the inner capsule wall. One embodiment of the vital sign monitor includes optical oscillometric circuit means responsive to an output signal from the optical sensor for determining systolic pressure, mean pressure and diastolic pressure during a transition in capsule pressure between a pressure greater than normal systolic pressure and a pressure less than normal diastolic pressure.

24 Claims, 4 Drawing Sheets

U.S. PATENT DOCUMENTS

| | | | |
|---|---|---|---|
| 4,860,759 | A | 8/1989 | Kahn et al. |
| 4,867,170 | A | 9/1989 | Takahashi |
| 4,869,261 | A | 9/1989 | Peňáz |
| 5,052,397 | A | 10/1991 | Ramsey et al. |
| 5,111,817 | A * | 5/1992 | Clark et al. ............... 600/323 |
| 5,170,795 | A | 12/1992 | Ramsey et al. |
| 5,237,997 | A | 8/1993 | Greubel et al. |
| 5,261,414 | A | 11/1993 | Aung et al. |
| 5,273,036 | A | 12/1993 | Kronberg et al. |
| 5,368,039 | A | 11/1994 | Moses |
| 5,431,170 | A | 7/1995 | Mathews |
| 5,485,838 | A * | 1/1996 | Ukawa et al. ............. 600/330 |
| 5,505,207 | A | 4/1996 | Abbs et al. |
| 5,529,755 | A | 6/1996 | Higashio et al. |
| 5,606,977 | A | 3/1997 | Ramsey et al. |
| 5,676,139 | A | 10/1997 | Goldberger et al. |
| 5,776,071 | A | 7/1998 | Inukai et al. |
| 5,827,181 | A | 10/1998 | Dias et al. |
| 5,830,137 | A | 11/1998 | Scharf |
| 5,860,919 | A * | 1/1999 | Kiani-Azarbayjany et al. ............ 600/322 |
| 5,891,021 | A | 4/1999 | Dillon et al. |
| 6,080,110 | A | 6/2000 | Thorgersen |
| 6,106,478 | A | 8/2000 | Tochikubo et al. |
| 6,149,588 | A | 11/2000 | Noda et al. |
| 6,178,342 | B1 * | 1/2001 | Borgos et al. ............. 600/322 |
| 6,213,952 | B1 | 4/2001 | Finarov et al. |
| 6,340,349 | B1 | 1/2002 | Archibald et al. |
| 6,440,082 | B1 | 8/2002 | Joo et al. |
| 6,572,636 | B1 | 6/2003 | Hagen et al. |
| 6,801,798 | B1 * | 10/2004 | Geddes et al. ............. 600/323 |
| 2002/0165595 | A1 | 11/2002 | Dupelle et al. |
| 2002/0188210 | A1 | 12/2002 | Aizawa |
| 2003/0060723 | A1 | 3/2003 | Joo et al. |
| 2004/0116969 | A1 | 6/2004 | Owen et al. |
| 2005/0043763 | A1 | 2/2005 | Marcovecchio et al. |

FOREIGN PATENT DOCUMENTS

| | | |
|---|---|---|
| WO | WO2004/073787 | 9/2004 |

OTHER PUBLICATIONS

Earl H. Wood, M.D., Ph.D., Julian R. B. Knutson, M.D. and Bowen E. Taylor, M.D., "Measurement of Blood Content and Arterial Pressure in the Human Ear," *Staff Meetings of the Mayo Clinic*, Jul. 5, 1950, pp. 398-405.

Geddes, L.A., M.E., Ph.D., *The Direct and Indirect Measurement of Blood Pressure*, 1970,Year Book Medical Publishers, Inc., Chicago, Illinois, pp. 70-99.

John W. Severinghaus, M.D. and Yoshiyuki Honda, M.D., "History of Blood Gas Analysis. VII. Oximetry," *Journal of Clinical Monitoring*, Apr. 1987, pp. 135-138, vol. 3, No. 2.

Ken-ichi Yamakoshi, Hideaki Shimazu and Tatsuo Togawa, "Indirect Measurement of Instantaneous Arterial Blood Pressure in the Human Finger by the Vascular Unloading Technique," *IEEE Transactions on Biomedical Engineering*, Mar. 1980, pp. 150-155, vol. BME-27, No. 3.

L. A. Geddes, M. Voelz, C. Combs, D. Reiner and C. F. Babbs, "Characterization of the Oscillometric Method for Measuring Indirect Blood Pressure," *Annals of Biomedical Engineering—The Journal of the Biomedical Engineering Society*, 1982, pp. 271-280, vol. 10, Pergamon Press Ltd., United States.

L. A. Geddes, M.E., Ph.D., *The Direct and Indirect Measurement of Blood Pressure*, 1970, Year Book Medical Publishers, Inc., Chicago, Illinois, United States, pp. 70-98, 135-145.

L. A. Geddes, ME, PhD, *Handbook of Blood Pressure Measurement*, 1991, The Humana Press, Inc., Clifton, New Jersey, United States, pp. 88-107.

L.A. Geddes, "Heritage of the Tissue-Bed Oximeter," *IEEE Engineering in Medicine and Biology*, Mar./Apr. 1997, pp. 87-91.

Maynard Ramsey III, "Noninvasive Automatic Determination of Mean Arterial Pressure," *Medical & Biological Engineering & Computing—Journal of the International Federation for Medical & Biological Engineering*, Jan. 1979, pp. 11-18, vol. 17, No. 1.

Nuhr et al., "Forehead $SpO_2$ Monitoring Compared to Finger $SpO_2$ Recording in Emergency Transport," *Anaesthesia*, 2004, vol. 59, pp. 390-393.

Patrick G. Yong, BSEE, and Leslie A. Geddes, ME, PhD, FACC, "The Effect of Cuff Pressure Deflation Rate on Accuracy in Indirect Measurement of Blood Pressure With the Auscultatory Method," *Journal of Clinical Monitoring*, Jul. 1987, pp. 155-159, vol. 3, No. 3.

Posey et al., "The Meaning of the Point of Maximum Oscillations in Cuff Pressure in the Direct Measurement of Blood Pressure," Part 1, *Cardiovascular Research Center Bulletin.*, 1969, pp. 15-25, vol. 8, No. 1.

Sokwoo Rhee, Boo-Ho Yang and Haruhiko Harry Asada, "Artifact-Resistant Power-Efficient Design of Finger-Ring Plethysmographic Sensors," *IEEE Transactions on Biomedical Engineering*, Jul. 2001, pp. 795-805, vol. 48, No. 7.

Tyco Healthcare advertisement for Max-Fast Forehead Sensor.

Tyco Heathcare advertisement for N-595 Pulse Oximeter.

Zijlstra, Willem Gerrit, *Fundamentals and Applications of Clinical Oximetry*, Van Gorcum & Comp. N.V., c. 1951 (cover and 2 pages).

* cited by examiner

OPTICAL NONINVASIVE VITAL SIGN MONITOR

CROSS-REFERENCE TO RELATED APPLICATION

This application claims the benefit of U.S. Provisional Patent Application Ser. No. 60/581,584 filed Jun. 21, 2004, which application is hereby incorporated by reference.

BACKGROUND OF THE INVENTION

This invention relates to the noninvasive measurement of parameters such as blood pressure, heart and respiratory rate and oxygen saturation in man and animals, and more particularly to the optical noninvasive measurement of blood parameters.

A number of noninvasive methods of measuring blood parameters are known. For example, blood pressure has been measured by the auscultatory method which uses a cuff and a stethoscope or microphone, and by the oscillometric method which only requires a cuff applied to a body member. The conventional oscillometric method relies on the small-amplitude pulsatile pressure oscillations communicated to the cuff by the underlying artery in the body member during cuff deflation from above systolic pressure to zero pressure. Such arterial pressure oscillations cause corresponding oscillations in cuff pressure which can be amplified and used to identify systolic, mean and diastolic pressure. For example, it has been established by Posey et al. that the cuff pressure for maximal amplitude oscillations corresponds to mean arterial pressure. See Posey et al., "The Meaning of the Point of Maximum Oscillations in Cuff Pressure in the Direct Measurement of Blood Pressure," Part 1, *Cardiovascular Res. Ctr. Bull.* 8(1):15–25, 1969. See also Ramsey, "Noninvasive Automatic Determination of Mean Arterial Pressure," *Med. Biol. Eng. Comput.* 17:17–18, 1979; and Geddes et al., "Characterization of the Oscillometric Method for Measuring Indirect Blood Pressure," *Annals of Biomedical Engineering*, Vol. 10, pp. 271–280, 1982. All such references are incorporated herein by reference.

Commercially available oscillometric devices are useful for some applications but are not particularly suited for use on a subject's forehead, for example. A need exists for improvements in vital sign monitors to enable reliable monitoring with noninvasive sensor units which can be quickly applied to a subject during and after cardiopulmonary resuscitation (CPR), during transport, or during surgery or other procedures in conscious and anesthetized subjects.

SUMMARY OF THE INVENTION

The present invention meets the above need and others and provides significant advantages with an optical noninvasive vital sign monitor comprising a reflectance-type optical sensor within a pressurizable capsule retained by a band or other restraint, the capsule having an optically transparent or translucent inner wall adapted for placement against a subject's skin. The optical sensor is mounted on the inside surface of the pressurizable capsule's inner wall, that is, the wall which contacts the subject's skin during use, and includes a light source and a photodetector aimed toward the inside surface of the inner capsule wall. Such internal mounting of the sensor provides a smooth contact with the skin surface and facilitates an even pressure distribution by the capsule.

According to one aspect of the present invention, the vital sign monitor includes optical oscillometric circuit means responsive to an output signal from the optical sensor for determining systolic pressure, mean pressure and diastolic pressure during a transition in capsule pressure between a pressure greater than normal systolic pressure and a pressure less than normal diastolic pressure, i.e., a transition through a range exceeding the range that spans the systolic and diastolic pressures that would be considered normal in a subject for which the monitor is designed to be used The objects and advantages of the present invention will be more apparent upon reading the following detailed description in conjunction with the accompanying drawings.

DETAILED DESCRIPTION OF PREFERRED EMBODIMENTS

Figure 1:
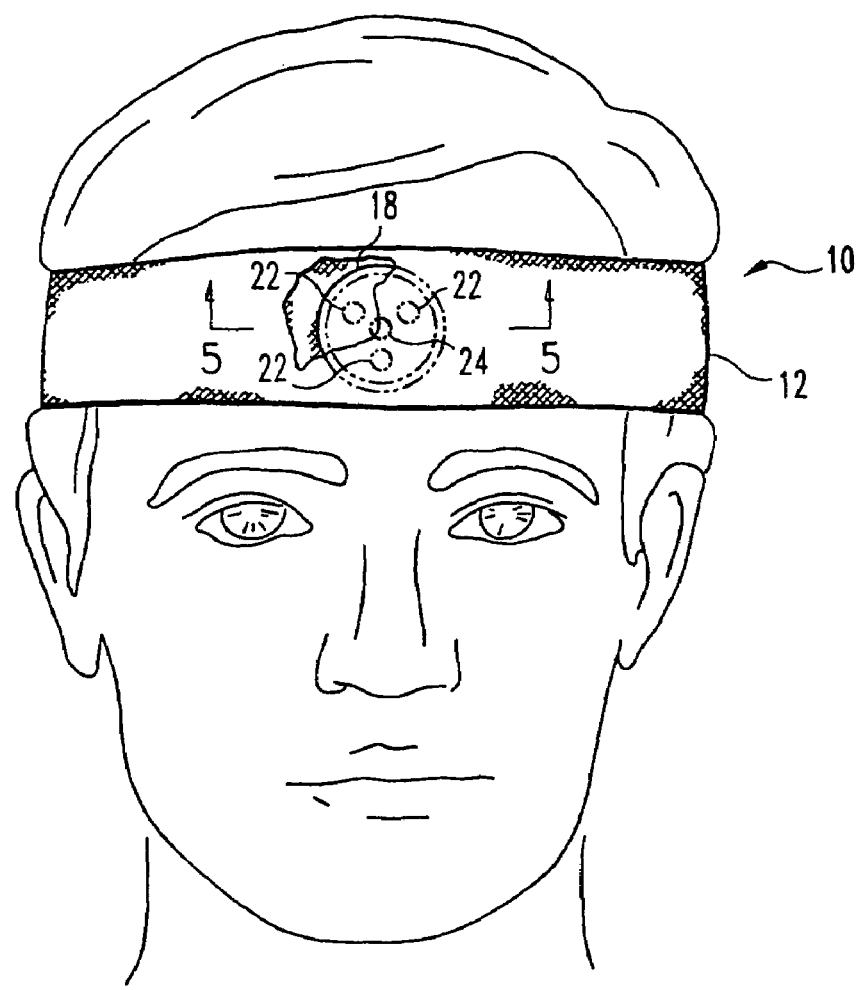
FIG. 1 is a diagram of one embodiment of a forehead-mounted optical noninvasive sensor unit according to the present invention, shown in position on a human subject, with a headband partially cut away to reveal a portion of a pressurizable capsule.

For the purpose of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device and such further applications of the principles of the invention as illustrated therein being contemplated as would normally occur to one of ordinary skill in the art to which the invention relates.

An optical sensor in accordance with the present invention is useful in certain applications on various body sites, such as the chest, leg or arm, e.g., the wrist, but one preferred embodiment is a forehead-mounted unit.

FIGS. 1–5 illustrate one embodiment of a forehead-mounted optical noninvasive multifunction sensor unit 10 according to the present invention. A headband 12 made of a relatively inelastic flexible fabric and having a Velcro® tab or other suitable fastener 14 on each end has a pocket 16 formed therein to accommodate a pressurizable capsule 18 having one or more reflectance-type optical sensors 20 mounted therein. In one preferred embodiment, the optical sensor includes a plurality of LEDs 22 symmetrically spaced around photodetector 24, while other embodiments have a plurality of photodetectors surrounding one or more LEDs. Significantly, the optical sensor is mounted on the inside surface 26 of the pressurizable capsule's inner wall 28, that is, the wall which contacts the subject's forehead during use. Such mounting provides a smooth contact surface with the forehead and facilitates an even pressure distribution.

Figure 2:
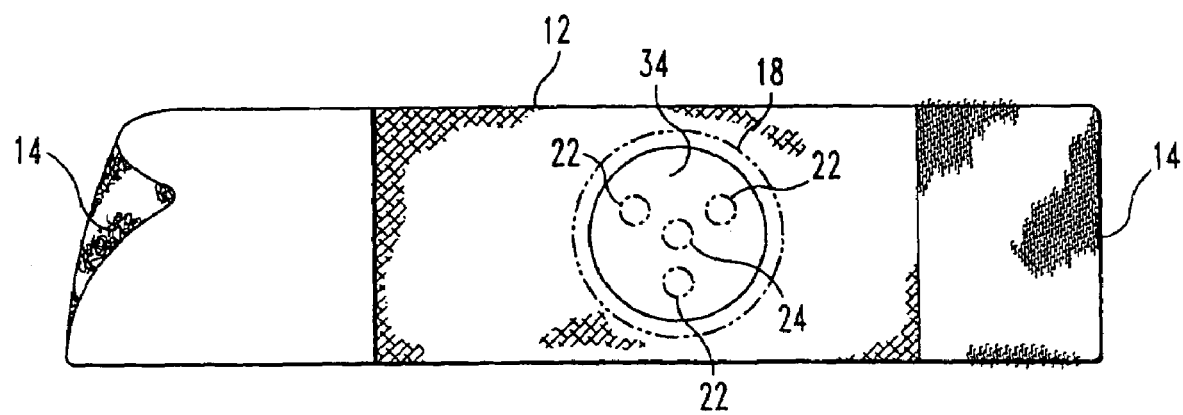
FIG. 2 illustrates the sensor unit of FIG. 1 with the headband unrolled, shown from the side facing the subject's forehead during use.
Figure 5:
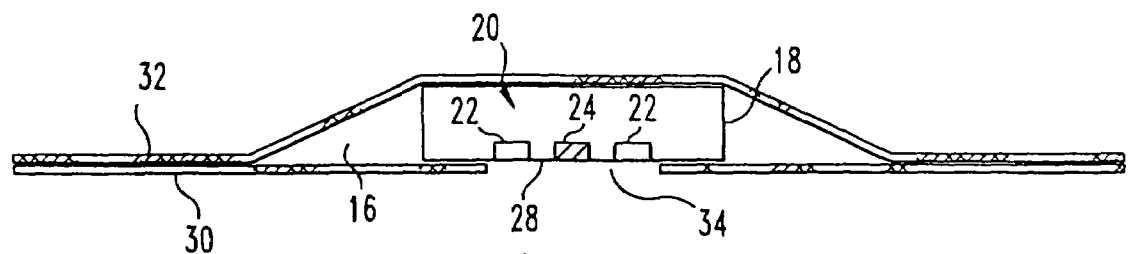
FIG. 5 is a cross-section of the sensor unit taken along line 5—5 of FIG. 1.

Capsule 18 or at least its inner wall 28 is made of a smooth optically transparent material. The transmittance of the material is preferably greater than 50% at the wavelength(s) of light emitted by the LEDs. The capsule may have a wall thickness of approximately 0.010 inches. PVC or silicone is presently preferred, although latex and polyurethane or other materials are also suitable to varying degrees. The headband may have elongated inner and outer layers 30 and 32, respectively, or may have multiple layers only where desired for the pocket, which may have a circular or rectangular hole or window 34 through its inner layer 30 as shown in FIGS. 2 and 5. LEDs 22 and photodetector 24 are all affixed to the inside surface of capsule wall 28 so as to be optically aligned with the opening 34 and thereby with the forehead of a subject when the headband is in position on the subject's head.

Preferably, the LED(s) and photodetector(s) directly contact the inside surface of wall 28 and are affixed thereto with an optically clear adhesive, e.g., Superglue or other adhesive suitable for the particular material used for the capsule. The LEDs and photodetector may be affixed to wall 28 before the capsule is completely formed or sealed, and the capsule may then be sealed so as to enclose pneumatically the LEDs and photodetector. The LEDs and photodetector may be affixed to the capsule wall individually, or as a sub-assembly in which they are held together in desired relative positions by a flexible carrier or substrate, which is preferably spaced from the device surfaces which contact the capsule wall so as to facilitate flush mounting of those surfaces to the capsule wall. Mounting of the LED(s) and photodetector(s) inside the sealed pressurizable capsule facilitates the use of the device on wet or diaphoretic subjects because the transducers are protected from water and moisture.

Figure 3:
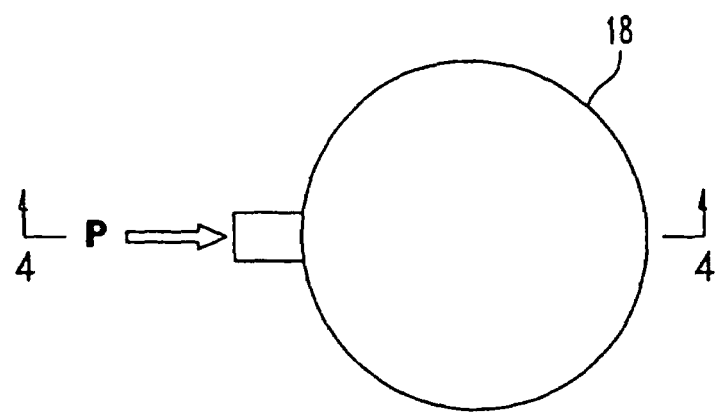
FIG. 3 is a front view of the pressurizable capsule of FIGS. 1 and 2.
Figure 4:
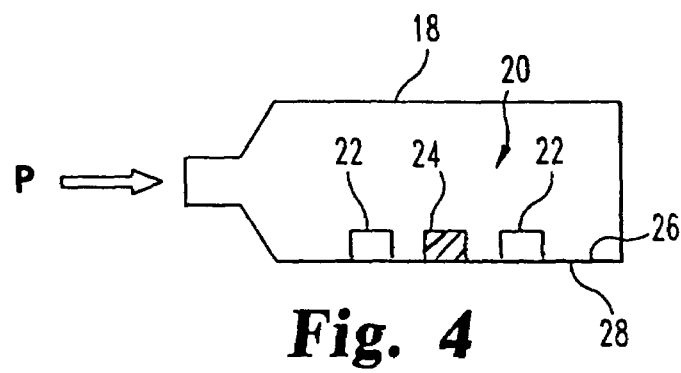
FIG. 4 is a cross-section of the pressurizable capsule taken along line 4—4 of FIG. 3, showing LEDs and a photodetector mounted within the capsule on the inside surface of the capsule wall which contacts the subject's forehead.

Headband 12, not drawn to scale in FIG. 2, is sized to extend around the head of the subject and, for an adult subject, may have a height (vertical dimension in the plane of FIG. 2) of approximately 2 inches on the subject's forehead. In one preferred embodiment, outer layer 32 is an inelastic band or strap extending around the subject's head, while inner layer 30 extends only the length of the pocket and may be somewhat elastic or loosely fitted to outer layer 32 so as to allow for expansion of the pocket upon inflation of the pressurizable capsule contained therein. The capsule may have a circular cross-section as shown in the drawings, with a diameter of approximately 1 to 2 inches, preferably approximately 1.75 inches, for an adult, and is provided with a pressure port (P) as depicted in FIGS. 3 and 4. In one alternative embodiment the capsule is a substantially rectangular bladder, approximately 1.75 inches high and 4 inches long for an adult. The capsule size is proportionately smaller for smaller subjects, e.g., pediatric patients. The diameter of the window in layer 30 is smaller than the capsule height, as shown in the drawings. The window may alternatively be in the shape of a horizontal slot or other shape suitable for the arrangement of optical sensor components. The window may be a transparent part of inner layer 30, or the entire inner layer may be transparent.

Blood pressure, including systolic, mean and diastolic pressures, can be obtained with optical sensor unit 10 from the amplitude spectrum of the pulses obtained during deflation of capsule 18 from a suprasystolic pressure to zero pressure, as described below. Monochromatic LEDs are suitable for monitoring blood pressure. For example, the transducer may employ infrared LEDs such as PDI-E801 or PDI-E804, 880 nm LEDs available from Photonic Detectors, Inc. The LEDs and photodetector are preferably matched to operate at the same desired wavelength. One example of a suitable photodetector is a Fairchild Semiconductor QSD723 phototransistor, with a peak sensitivity at 880 nm. Another suitable operating wavelength for the LEDs and photodetector is 805 nm, at which wavelength the blood pressure pickup has no oxygen-saturation error, as will be appreciated from the discussion of oximetry below. An advantage of either of the example wavelengths is that there are virtually no environmental light sources in this infrared region.

Figure 6:
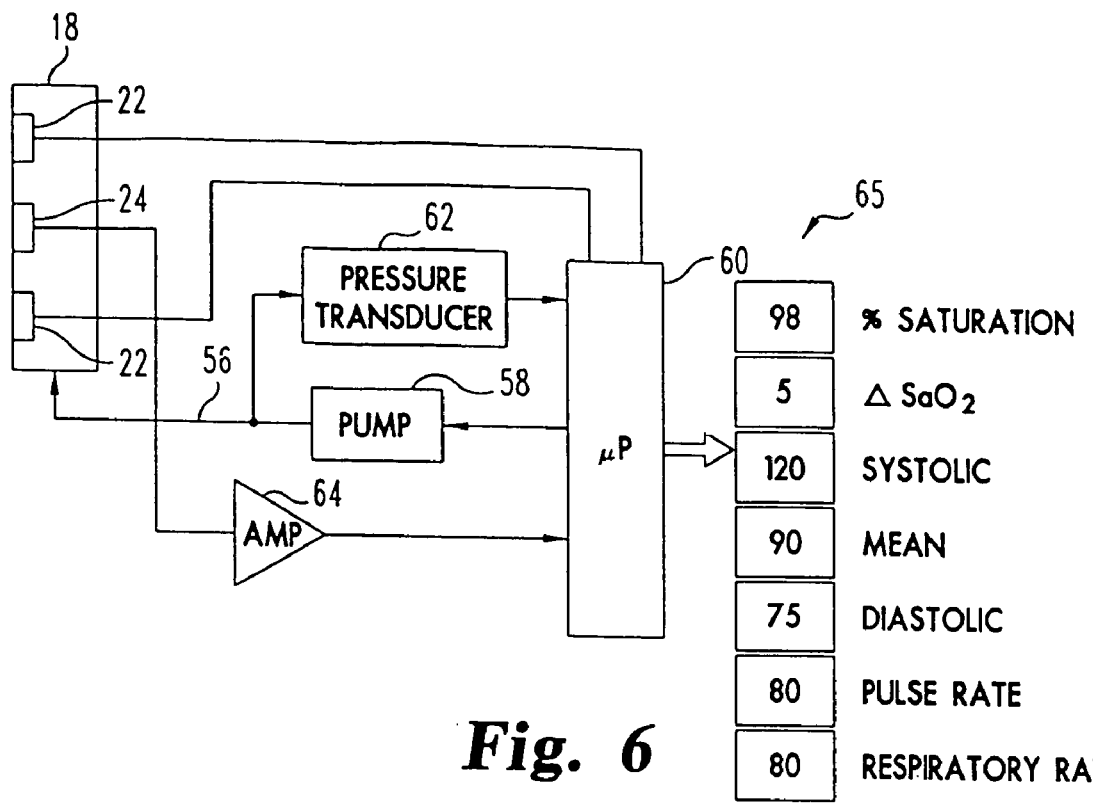
FIG. 6 is a block diagram of one embodiment of an optical noninvasive vital sign monitor according to the present invention.

Referring to FIG. 6, pressurizable capsule 18 is connected by an inflation tube 56 to a pump 58 which is controlled by a microprocessor 60. Pressure in the line to the pressurizable capsule is measured by means of a pressure transducer 62 having a signal output connected to the microprocessor. Suitable transducers are available from Cobe Labs, Littleton, Colo. A/D conversion may be provided in the microprocessor or in the transducer or with a second A/D converter provided between the two. The microprocessor controls the LEDs and, during blood pressure measurement, may be programmed to energize the LEDs simultaneously. The photodetector produces an output signal which is supplied to the microprocessor through an amplifier 64. The amplified photodetector output signal is converted to digital form in the microprocessor itself if the microprocessor has an internal A/D converter, or in a separate A/D converter provided between the amplifier and the microprocessor. The LEDs may be energized continually, or digital pulsing with synchronous detection can be used to minimize detection artifacts and maximize battery life by pulsing the LEDs.

The microprocessor is suitably programmed to identify, based on the digitized output signal of the photodetector, the points in the capsule pressure signal which correspond to systolic, mean and diastolic pressure, and displays the corresponding values on a display 65 which may comprise separate indicators as shown in FIG. 6, or may provide an output for distant recording. The blood pressure readings correspond to blood pressure in the forehead, which is different than blood pressure in the arm, for example. Thus, the monitor may be said to perform site blood pressure measurement.

Figure 7:
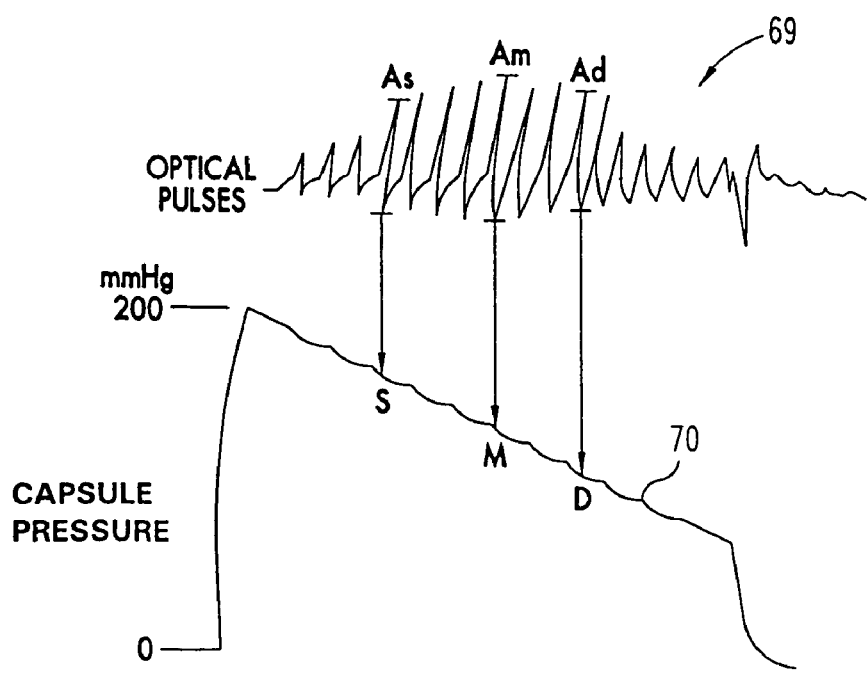
FIG. 7 is a set of sample waveforms illustrating optical oscillometric blood pressure measurement with a vital sign monitor according to the present invention.

Blood pressure is measured during a transition in capsule pressure between a selected suprasystolic pressure and zero pressure. The transition may be an upward or downward transition but is described below in terms of a gradual downward transition such as shown in FIG. 7, which shows a sample optical pulse waveform 69 obtained during a capsule pressure cycle represented by curve 70, which is marked to indicate the points corresponding to systolic (S), mean (M), and diastolic (D) pressure. When capsule pressure is raised above systolic pressure, all oscillations are extremely small. As pressure in the capsule falls below systolic pressure, the pulses increase, and as the pressure is reduced further, the optical pulse amplitude increases further and reaches a maximum, labeled $A_m$ in FIG. 7, at which point the capsule pressure is equal to mean arterial pressure, labeled M in FIG. 7. With a continued decrease in capsule pressure, the oscillation amplitude decreases and returns to a uniform level.

The peak-to-peak amplitudes of the optical pulse waveform at the points coinciding with the occurrence of systolic and diastolic pressure are designated respectively as $A_s$ and $A_d$ in FIG. 7. Those amplitudes are calculated as predetermined percentages of $A_m$, and the corresponding points in time are identified on the optical pulse waveform, by interpolation if necessary between adjacent pulses, after which the values of capsule pressure at those points in time are identified as systolic (S) and diastolic (D) pressure, respectively. Appropriate percentages or ratios are determined experimentally. For optical sensor unit 10 as described above applied to the forehead of an adult human subject of average height and weight, systolic pressure occurs when the amplitude ratio $A_s/A_m$ is approximately 0.5; diastolic pressure occurs with a ratio of $A_d/A_m$ of approximately 0.8; these algorithms depend on capsule height.

Systolic pressure may alternatively be calculated as a function of both $A_m$ and $P_m$, the mean capsule pressure, rather than on the basis of a fixed percentage of $A_m$. That is, the microprocessor may calculate $A_s$, the optical pulse amplitude corresponding in time with systolic pressure, according to an algorithm which includes mean capsule pressure as a factor. The following equation represents one form of such an algorithm:

$$A_s = A_m(a - b\, P_m)$$

where a and b are experimentally determined constants.

Heart rate can be obtained by counting the optical pulses when the capsule is not pressurized. Respiratory rate can also be obtained when the capsule is not pressurized, from the rhythmic changes in the amplitude of the optical pulses, as described in co-pending patent application Ser. No. 10/176,186, entitled Body-Member-Illuminating Pressure Cuff For Use In Optical Noninvasive Measurement Of Blood Parameters, filed Jun. 20, 2002, which patent application is hereby incorporated by reference.

Figure 8:
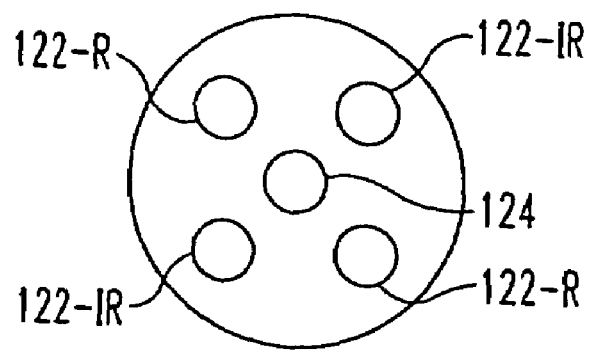
FIG. 8 is a front view of one embodiment of an optical sensor for oxygen saturation measurement with a vital sign monitor according to the present invention.

Referring again to FIG. 6, the vital sign monitor may have LEDs 22 which operate at different wavelengths for oxygen saturation measurement. Blood oxygen saturation is defined as the ratio of oxygenated hemoglobin ($HbO_2$) to the total hemoglobin ($Hb + HbO_2$), and is typically expressed as a percentage. The oximeter determines oxygen saturation ($SaO_2$) by measuring the optical transmission at two wavelengths of light passing through a tissue bed. Although other wavelengths are contemplated, it is presently preferred to operate at wavelengths of approximately 650 nm and 805 nm for oxygen saturation measurement. As shown in the above-referenced co-pending patent application Ser. No. 10/176,186, hemoglobin (Hb) has negligible transmission at 650 nm, and hemoglobin (Hb) and oxygenated hemoglobin ($HbO_2$) transmit equally well at 805 nm; the latter wavelength is known as the isobestic point. That is, the transmission at 805 nm is independent of oxygen saturation. As adapted for oximetry, the optical sensor may have two pairs of diametrically opposed LEDs: a pair of red-emitting LEDs, preferably emitting at approximately 650 nm, and a pair of infrared-emitting LEDs, preferably emitting at approximately 805 nm. Red (R) and infrared (IR) LED pairs 122-R and 122-IR may be arranged on perpendicular axes as shown in FIG. 8, with a photodetector 124 in the center of the LEDs as in the first embodiment. As an alternative to separate narrowband LEDs, a red LED and infrared LED may be combined in one multi-wavelength LED such as type Epitex L660/805/975-40D00, available from Epitex, Kyoto, Japan. Three such multi-wavelength LEDs may be arranged as in FIG. 1 if desired.

The red LEDs are switched on while the infrared LEDs are switched off, and vice versa, and the photodetector output signal is supplied to the microprocessor for processing as described above. The photodetector may be a broadband detector, such as that identified above, that detects reflected light from the red-emitting LED when that LED is energized and then detects reflected infrared radiation from the infrared LED when that LED is energized. The red and infrared LEDs are preferably energized alternately in rapid succession, e.g., at a rate of 200 pulses per second or more. This technique permits the use of high-intensity short-duration pulses. Synchronous detection is used to achieve the highest signal-to-noise ratio. Two benefits result: 1) a low average power and minimum heating, and 2) the system is less sensitive to stray ambient illumination. The red and infrared signals are sampled and processed to obtain $SaO_2$, which may then be displayed on display 65 of the monitor shown in FIG. 6. A short display response time and analog and digital outputs may be provided for connection to auxiliary equipment.

A baseline for measurement may be established by first inflating the capsule to a high pressure sufficient to squeeze all of the blood out of the blood vessels under the capsule and thus out of the optical path. For example, the capsule pressure may be held at a maximum pressure for a desired time to obtain the bloodless transmission reading, which can be assigned a value of 100% transmission. When the capsule pressure is released, blood enters the optical path and the red and infrared transmissions are measured. The optical density is computed for each of the transmitted signals, and the ratio of red to infrared optical density is calculated and scaled to provide an output value corresponding to the percentage of oxygen saturation.

Figure 9:
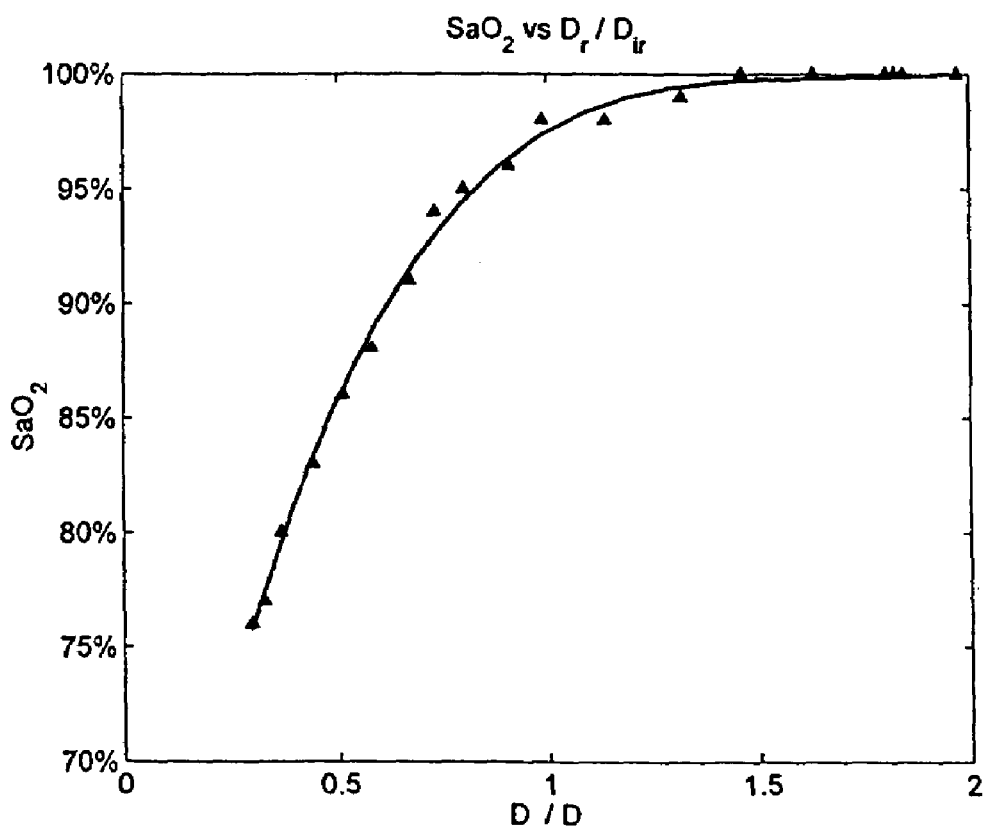
FIG. 9 is an example of a calibration curve for use in oxygen saturation measurement.

Beer's law relates the optical density (D) to the concentration of a dissolved substance. Optical density (D) is equal to ln 1/T, where T is the transmittance. Therefore the oxygen saturation ($SaO_2$) is given by:

$$SaO_2 = \frac{AD_R}{D_{IR}} + B$$

where A and B are constants. This equation predicts a linear relationship based on Beer's law. However, Beer's law applies to solutions in which the absorbing substance is dissolved. Blood is a suspension, and, consequently, the relationship between $SaO_2$ and the ratio of the optical density for red and infrared radiation is nonlinear, as shown in FIG. 9. Between 30% and 60% saturation, the relationship is almost linear; above this range the relationship is nonlinear. The curve in FIG. 9 is an example of a suitable calibration curve which may be programmed into the microprocessor, e.g., in the form of a lookup table, for calculation of $SaO_2$. Further information regarding methods of measuring blood oxygen saturation may be found in the following references which are hereby incorporated by reference: Geddes, "Heritage of the Tissue-Bed Oximeter," *IEEE Engineering in Medicine and Biology*, 87–91, March/April 1997; Geddes and Baker, *Principles of Applied Biomedical Instrumentation*, 3$^{rd}$ ed., Wiley, New York, 1989.

Calibration of the oximeter also involves balancing the outputs for the red and infrared channels to obtain the same optical sensitivity for both, and ensuring that both channels have a linear response to the red and infrared radiation. Optical filters can be used as calibration standards.

In another embodiment, an optical sensor within a pressurizable capsule as described above is placed on the subject's chest and restrained by a band, preferably a relatively inflexible band, around the subject's torso at chest height. For example, the optical sensor may be positioned over the manubrium (top of the sternum), or along the sternum to the xiphoid (bottom end of the sternum), where a substantially flat bone underlies the tissue bed and reflects incident radiation from the light source. The pressurizable capsule may be contained within a pocket in the band such as described above with respect to FIGS. 1–5, and the pocket may be sealed or may have an opening to allow for removal and replacement of the capsule.

The restraint may be a band extending completely around the body member, or for certain applications the pressurizable capsule may be restrained by an adhesive strip or pad adapted to adhere to the skin adjacent to the desired sensor location; the restraint is designed to hold the capsule against the skin sufficiently to allow the capsule, when inflated, to apply pressure to the skin and compress the arterial blood supply in the tissue bed. While not preferred, it may be suitable in certain applications to restrain the capsule by other means, such as by placing it under the weight of a subject, e.g., in contact with the back of a patient in a supine position. As noted above, an optical sensor in accordance with the present invention is useful in certain applications on various body sites, such as the chest, leg or arm.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

We claim:

1. An optical noninvasive sensor unit, comprising:
   a pressurizable capsule having an optically transparent or translucent inner wall adapted for placement against a skin surface of a subject over a tissue bed containing an arterial blood supply, said capsule having an expanded state and an unexpanded state;
   a reflectance-type optical sensor mounted within said pressurizable capsule on the inside surface of said inner wall, said optical sensor including a light source and a photodetector aimed toward said inside surface of said inner wall; and
   a restraint for restraining said capsule against the skin during said expanded state so as to allow said capsule to compress the arterial blood supply.

2. The sensor unit of claim 1, wherein said restraint includes a band adapted for placement around a body part of the subject.

3. The sensor unit of claim 2, wherein said band includes a pocket which contains said capsule.

4. The sensor unit of claim 3, wherein said band is a headband.

5. The sensor unit of claim 4, wherein said light source comprises at least three LEDs equally spaced around said photodetector within said capsule.

6. The sensor unit of claim 2, wherein said band is adapted for placement around the subject's chest.

7. An optical noninvasive vital sign monitor, comprising:
   a pressurizable capsule having an optically transparent or translucent inner wall adapted for placement against a skin surface of a subject over a tissue bed containing an arterial blood supply, said capsule having an expanded state and an unexpanded state;
   a reflectance-type optical sensor mounted within said pressurizable capsule on the inside surface of said inner wall, said optical sensor including a light source and a photodetector aimed toward said inside surface of said inner wall;
   a restraint for restraining said capsule against the skin during said expanded state so as to allow said capsule to compress the arterial blood supply; and
   a processing circuit connected to said light source and photodetector for measuring blood pressure.

8. The vital sign monitor of claim 7, wherein said processing circuit includes means connected to said light source and photodetector for measuring blood oxygen saturation.

9. The vital sign monitor of claim 8, further comprising pump means for supplying gas under pressure to said capsule.

10. The vital sign monitor of claim 9, wherein said processing circuit further includes optical oscillometric circuit means responsive to an output signal from said optical sensor for determining systolic pressure, mean pressure and diastolic pressure during a transition in capsule pressure between a pressure greater than normal systolic pressure and a pressure less than normal diastolic pressure.

11. The sensor unit of claim 10, wherein said restraint includes a band adapted for placement around a body part of the subject.

12. The sensor unit of claim 11, wherein said band includes a pocket which contains said capsule.

13. The sensor unit of claim 12, wherein said band is a headband.

14. The sensor unit of claim 13, wherein said light source comprises at least three LEDs equally spaced around said photodetector within said capsule.

15. The sensor unit of claim 11, wherein said band is adapted for placement around the subject's chest.

16. An optical noninvasive method of monitoring vital signs, comprising:
   providing a reflectance-type optical sensor having a light source and a photodetector entirely within a pressurizable capsule having an optically transparent or translucent inner wall, said light source and photodetector aimed toward the inside surface of said inner capsule wall, said capsule having an expanded state and an unexpanded state;
   placing said capsule on a body part of a subject with said inner wall of said capsule over a tissue bed containing an arterial blood supply and overlying a bone surface which reflects incident light, said light source and photodetector being spaced apart from the subject's skin by said inner wall of said capsule;
   restraining said capsule against the skin during said expanded state so as to allow said capsule to compress the arterial blood supply; and
   measuring blood pressure based on signals from said photodetector.

17. The method of claim 16, further comprising measuring blood oxygen saturation based on signals from said photodetector.

18. The method of claim 17, further comprising supplying gas under pressure to said capsule.

19. The method of claim 18, wherein said blood pressure measurement is performed by determining systolic pressure, mean pressure and diastolic pressure during a transition in capsule pressure between a pressure greater than normal systolic pressure and a pressure less than normal diastolic pressure, and wherein said determining is performed using an optical oscillometric method.

20. The method of claim 19, wherein said capsule is restrained by a band placed around a body part of the subject.

21. The method of claim 20, wherein said band includes a pocket which contains said capsule.

22. The method of claim 21, wherein said band is a headband.

23. The method of claim 22, wherein said light source comprises at least three LEDs equally spaced around said photodetector within said capsule.

24. The method of claim 20, wherein said band is adapted for placement around the subject's chest.

* * * * *

UNITED STATES PATENT AND TRADEMARK OFFICE
CERTIFICATE OF CORRECTION

| | | |
|---|---|---|
| PATENT NO. | : 7,164,938 B2 | Page 1 of 1 |
| APPLICATION NO. | : 11/157215 | |
| DATED | : January 16, 2007 | |
| INVENTOR(S) | : Leslie A. Geddes et al. | |

It is certified that error appears in the above-identified patent and that said Letters Patent is hereby corrected as shown below:

Col. 1, Line 10, Insert:

--GOVERNMENT RIGHTS

This invention was made with government support under Grant No. #5 R21 EB001540-03 awarded by the National Institutes of Health. The government has certain rights in the invention.--

Signed and Sealed this

First Day of July, 2008

JON W. DUDAS
*Director of the United States Patent and Trademark Office*